United States Patent [19]
Takahashi et al.

[11] Patent Number: 5,643,775
[45] Date of Patent: Jul. 1, 1997

[54] TREHALOSE PHOSPHORYLASE AND PREPARATION THEREOF

[75] Inventors: Eisaku Takahashi, Tokyo; Eiichi Takahashi; Kohki Saitoh, both of Iwaki; Toshihiko Wada, Tokyo; Yutaka Konai, Machida, all of Japan

[73] Assignee: Kureha Chemical Industry Co., Ltd., Japan

[21] Appl. No.: 406,554

[22] Filed: Mar. 20, 1995

[30] Foreign Application Priority Data

Mar. 23, 1994 [JP] Japan .................. 6-076461

[51] Int. Cl.$^6$ .................................................. C12N 9/10
[52] U.S. Cl. ............................................... 435/193
[58] Field of Search ...................................... 435/193

[56] References Cited

FOREIGN PATENT DOCUMENTS

| | | | |
|---|---|---|---|
| 0 639 645 A1 | 2/1995 | European Pat. Off. | C12P 19/12 |
| 6189779 | 7/1994 | Japan . | |
| WO95/01446 | 1/1995 | WIPO | C12N 15/82 |

OTHER PUBLICATIONS

Sharon L. Haynie et al., "Enzyme–Catalyzed Organic Synthesis of Sucrose and Trehalose with In Situ Regeneration of UDP–Glucose", *Applied Biochemistry and Biotechnology*, 23:155–170 (1990).

Kathleen A. Killick, "A Radiometric Assay for Trehalose–6–Phosphate Synthetase", *Analytical Biochemistry*, 79:310–318 (1977).

Yutaka Kitamoto et al., "α–Glucose–1–Phosphate Formation by a Novel Trehalose Phosphorylase from *Flammulina Velutipes*", *FEMS Microbiology Letters*, 55:147–150 (1988).

L.R. Marechal et al., "Metabolism of Trehalose in *Euglena Gracilis*" *J. Biol. Chem.* 247 No. 10:3223–3228 (1972).

S.O. Salminen et al., "Enzymes of α,α–Trehalose Metabolism in Soybean Nodules" *Plant Physiol.* 81:538–541 (1986).

*Primary Examiner*—Herbert J. Lilling
*Attorney, Agent, or Firm*—Testa, Hurwitz & Thibeault, LLP

[57] ABSTRACT

This invention provides highly thermally stable trehalose phosphorylases. The trehalose phosphorylases of the present invention can be obtained from cultured mixture of microorganisms and are highly thermally stable, and produce α-D-glucose 1-phosphate and D-glucose by an action on trehalose and an inorganic phosphoric acid or salt thereof, or trehalose by an action on α-D-glucose 1-phosphate and D-glucose. This invention also relates to the process for the preparation of trehalose phosphorylase, and trehalose or α-D-glucose 1-phosphate with said trehalose phosphorylase.

5 Claims, 4 Drawing Sheets

TREHALOSE PHOSPHORYLASE AND PREPARATION THEREOF

FIELD OF THE INVENTION

This invention relates to a trehalose phosphorylase which is useful for the preparation of trehalose, particularly to a thermally stable trehalose phosphorylase, and preparation and use thereof.

BACKGROUND OF THE INVENTION

Heretofore, a trehalose phosphorylase derived from *Euglena gracilis* has been reported as EC 2.4.1.64 in Enzyme Nomenclature 1992 (Academic Press). Also, an enzyme derived from *Flammulina velutipes* which produces trehalose from α-glucose 1-phosphate and glucose has been reported as a trehalose phosphorylase (FEMS Microbiology Letters, 55, 147–150 (1988)).

However, the above mentioned trehalose phosphorylase derived from *Flammulina velutipes* has not sufficiently been purified due to its low stability. Therefore, no sufficient enzymic properties thereof have been known, for example, pH and temperature stability, optimal reaction temperature or molecular weight, furthermore, no sufficient data for the optimal reaction pH or substrate specificity has been reported. In addition, its productivity of trehalose from α-glucose 1-phosphate and glucose was unsatisfactory.

The trehalose phosphorylase disclosed as EC 2.4.1.64 in Enzyme Nomenclature 1992 (Academic Press) is a trehalose phosphorylase which produce trehalose from β-D-glucose 1-phosphate and D-glucose.

The inventors have been investigating to find a novel thermally stable trehalose phosphorylase which produces trehalose from α-D-glucose 1-phosphate and D-glucose and found that microorganisms of Grifola, Pleurotus, Lyophyllum, Lentinus, Agaricus, Trametes, Coriolus, Lenzites, Schizophyllum, Panus, Crepidotus, Laetiporus, Polyporellus, Favolus, Trichaptum, Oudemansiella, Naematoloma, Rhodophyllus, Gloeophyllum, Fomes, Ganoderma, Elfvingia, Fomitopsis, Armillariella, Lampteromyces, Pholiota, and Tricholoma genera can produce trehalose phosphorylases. The inventors also found that these trehalose phosphorylases obtained from the above mentioned cultured microorganisms are thermally stable and accomplished the present invention.

This invention is based on the findings of enzymes which produce trehalose from α-D-glucose 1-phosphate and D-glucose. The trehalose phosphorylases of the present invention exhibit clearly different substrate specificity from that of the known enzymes producing trehalose from β-D-glucose 1-phosphate and D-glucose shown above. The trehalose phosphorylases of the present invention can catalyze the reaction of α-D-glucose 1-phosphate with D-glucose to produce trehalose.

The thermally stable trehalose phosphorylases can be obtained as purified single enzymes for the first time by the present invention and their physicochemical properties were elucidated.

SUMMARY OF THE INVENTION

One object of the present invention is to provide a thermally stable trehalose phosphorylase producing trehalose from α-D-glucose 1-phosphate and D-glucose.

The other object of the present invention is to provide a process for the production of trehalose phosphorylases by culturing specific microorganisms having trehalose phosphorylase productivity and isolation of trehalose phosphorylases from the cultured mixture.

One further object of the present invention is to provide a process for the production of trehalose from α-D-glucose 1-phosphate and D-glucose with trehalose phosphorylases produced by the above mentioned specific trehalose phosphorylase producing microorganisms and/or thermally stable trehalose phosphorylases.

The other further object of the present invention is to provide a process for the production of α-D-glucose 1-phosphate from trehalose with trehalose phosphorylases produced by the above mentioned trehalose phosphorylase producing microorganisms and/or thermally stable trehalose phosphorylase.

DETAILED DESCRIPTION OF THE INVENTION AND PREFERRED EMBODIMENTS

Figure 1:
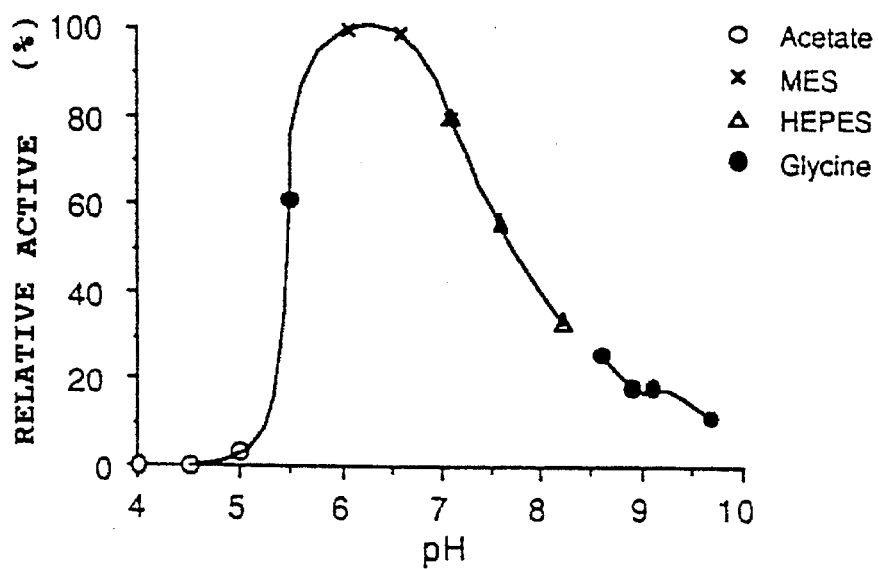
FIG. 1 shows the optimal pH range for the phosphorolysis with the trehalose phosphorylases of the present invention.

The trehalose phosphorylases obtained by the present invention have the following physicochemical properties.

1. Action:

Formation of trehalose from α-D-glucose 1-phosphate and D-glucose, hereinafter called as trehalose synthetic reaction. Formation of α-D-glucose 1-phosphate and D-glucose by the reaction of trehalose in the presence of an inorganic phosphoric acid, herein after called as phosphorolytic reaction.

2. Substrate specificity:

Action on trehalose as a disaccharide substrate in the phosphorolytic reaction. Action on α-D-glucose 1-phosphate and D-glucose as a sugar donor and as a sugar receptor, respectively, in the synthetic reaction.

3. Optimal reaction pH:

Trehalose synthetic reaction (35° C.)

pH at maximum activity: about 7.0 pH range exhibiting about 50% or over of maximum activity: 6.5–7.5

Phosphorolytic reaction (30° C.)

pH at maximum activity: 6.0–6.5 pH range exhibiting about 50% or over of maximum activity: 5.5–7.5

4. pH stability:
   Trehalose synthetic reaction: 5.0–10.0 (4° C., 24 hrs.)
   Phosphorolytic reaction: 5.5–9.5 (4° C., 24 hrs.)
5. Optimal reaction temperature range:
   Trehalose synthetic reaction (pH 7.0)
   Temperature at maximum activity: 35°–37.5° C.
   Temperature range at about 80% or over of maximum activity: 30°–40° C.
   Phosphorolytic reaction (pH 6.0)
   Temperature at maximum activity: 30°–35° C.
   Temperature range at about 80% or over of maximum activity: 25°–37.5° C.
6. Thermal stability:
   Trehalose synthetic reaction: stable at 35° C. for 30 min. (pH 7.0)
   Phosphorolytic reaction: stable at 35° C. for 30 min. (pH 6.0)
7. Inhibition with metal: inhibited with zinc and copper
8. Demand for metal: NO
9. Molecular weight: About 120,000 dalton (by GPC) About 60,000 dalton (by SDS-PAGE)

Trehalose phosphorylases which can produce trehalose from α-D-glucose 1-phosphate and D-glucose and have the above mentioned physicochemical properties have not been known and first reported by the present invention. Trehalose phosphorylase derived from Flammulina (FEMS Microbiology Letters, 55, 147–150 (1988)) was reported to exhibit optimal pH 6.3 in the trehalose synthetic reaction and optimal pH 7.0 in the trehalose phosphorolysis. The present inventors found that the trehalose phosphorylase derived from *Flammulina velutipes* is inactivated by warming treatment at 30° C. for 30 min. Therefore, the trehalose phosphorylases of the present invention are novel enzymes and different from that derived from Flammulina regarding thermal stability and optimal reaction pH.

The present inventors found that microorganisms of Grifola, Pleurotus, Lyophyllum, Lentinus, Agaricus, Trametes, Coriolus, Lenzites, Schizophyllum, Panus, Crepidotus, Laetiporus, Polyporellus, Favolus, Trichaptum, Oudemansiella, Naematoloma, Rhodophyllus, Gloeophyllum, Fomes, Ganoderma, Elfvingia, Fomitopsis, Armillariella, Lampteromyces, pholiota and Tricholoma genera can produce trehalose phosphorylases. Such enzymes have not been found in these microorganisms.

No process for the production of trehalose or α-D-glucose 1-phosphate with trehalose phosphorylases produced by the above mentioned microorganisms and/or thermally stable trehalose phosphorylases having the above mentioned physicochemical properties has been known.

The process for the preparation of trehalose phosphorylases of the present invention will be explained below. The microorganisms used invention in the present belong to genera of Grifola, Pleurotus, Lyophyllum, Lentinus, Agaricus, Trametes, Coriolus, Lenzites, Schizophyllum, Panus, Crepidotus, Laetiporus, Polyporellus, Favolus, Trichaptum, Oudemansiella, Naematoloma, Rhodophyllus, Gloeophyllum, Fomes, Ganoderma, Elfvingia, Fomitopsis, Armillariella, Lampteromyces, Pholiota or Tricholoma and any strain capable to produce trehalose phosphorylase and their mutants can be used. Furthermore, any microorganisms which can produce a trehalose phosphorylase having physicochemical properties shown above can be used.

The mutants of trehalose phosphorylase producing microorganisms can be obtained as shown below. Various generally used mutation inducers such as N-methyl-N'-nitro-N-nitrosoguanidine (NTG), ethyl methanesulfonate (EMS), and ultraviolet ray can be used to treat the above mentioned trehalose phosphorylase producing microorganisms to give their mutants.

The trehalose phosphorylases of the present invention can be produced by the cultivation of host transformed by insertion of a gene coded for the expression of trehalose phosphorylases or their modified enzymes having the above mentioned physicochemical properties into a suitable host. One method to obtain a gene coding trehalose phosphorylase having the above mentioned physicochemical properties can be illustrated as shown below. A DNA base sequence presumed from the amino acid sequence from N-terminal to about 20th amino acid in said trehalose phosphorylase is synthesized to give a DNA base sequence probe. The genomic DNA of microorganisms which codes trehalose phosphorylase and has the above mentioned physicochemical properties is in vitro packaged in λ phage such as EMBL3 to give a genomic library. Cloning of the gene coding said trehalose phosphorylase can be performed by the hybridization of the genomic library DNA with the aforementioned probe DNA. Then, the gene is inserted into a vector expressible in microorganisms such as Saccharomyces or Aspergillus genus to transform them. The transformed microorganisms are screened to give strains which can express the trehalose phosphorylase. In this way, the host cells which have the gene coded for the expression of trehalose phosphorylase can be obtained.

In the present invention, microorganisms which have the same or partially same immunochemical properties with that of the trehalose phosphorylase having the above mentioned physicochemical properties can also be used. The trehalose phosphorylase having the same or partially same immunochemical properties means a trehalose phosphorylase which give wholly or partially fused precipitin line with trehalose phosphorylase having physicochemical properties of the present invention by the known Ouchterlony double immunodiffusion method (Immunobiochemical Study Method, p.40, 1986, Pub. by Tokyo Kagaku Dozin Co., Ltd.).

Typical trehalose phosphorylase producing strains include microorganisms deposited in the National Institute of Bioscience and Human-Technology, Agency of Industrial Science and Technology, the Ministry of International Trade and Industry, Japan, and illustrated in Table 1.

Additionally, strains such as *Pleurotus cornucopiae* IFO 30528, *Laetiporus sulphureus* IFO 8406, *Laetiporus versisporus* IFO 9043, *Polyporellus picipes* IFO 30355, *Oudemansiella canarii* IFO 31216, *Ganoderma applanatum* IFO 6498, *Pholiota adiposa* IFO 9779, *Trametes hirsuta* ATCC 20561, *Trametes versicolor* ATCC 20547, *Coriolus consors* ATCC 20565, and *Coriolus pargamenus* ATCC 20562 can also be used.

Identification and nomenclature of these deposited strains are performed according to 'Colored Illustrations of Fungi of Japan' (1957, 1955 (addendum), and 'Illustrations of Mushrooms of Japan' (I (1987), II (1989), Rokuya Imaseki and Tsuguo Hongo, Pub. by Hoikusha Co., Ltd.), and 'Mycological Flora of Japan' (II , part 1, (1936), part 2 (1939), part 3 (1950), part 4 (1955), part 5 (1959), Seiya Ito, Pub. by Yokendo Ltd.).

The strains used in the present invention and deposited in National Institute of Bioscience and Human-Technology, Agency of Industrial Science and Technology, the Ministry of International Trade and Industry, Japan, were isolated and purified by partial transplantation of deteriorated plants adhered with these microorganisms, a tissue of fruiting body grown on plants, or spores on a suitable agar medium and 3–4 times subculture procedures at suitable temperatures for several weeks.

TABLE 1

| Microorganisms | Deposit No. |
|---|---|
| *Grifola frondosa* | FERM BP-35 |
| *Pleurotus ostreatus* | FERM P-1746, FERM BP-4951 |
| *Lyophyllum ulmarium* | FERM P-985, FERM BP-4940 |
| *Lentinus edodes* | FERM BP-947 |
| *Agaricus bisporus* | FERM P-1748, FERM BP-4952 |
| *Coriolus versicolor* | FERM P-2412, ATCC 20547 |
| *Coriolus hirsuta* | FERM P-2711, ATCC 20561 |
| *Coriolus consors* | FERM P-988, ATCC 20565 |
| *Lenzites betulina* | FERM BP-27 |
| *Schizophyllum commune* | FERM P-1744, FERM BP-4941 |
| *Panus rudis* | FERM BP-4588 |
| *Crepidotus variabilis* | FERM P-5161, FERM BP-4943 |
| *Favolus arcularius* | FERM BP-4590 |
| *Trichaptum biforme* | FERM P-2712, ATCC 20562 |
| *Naematoloma sublateritium* | FERM P-3051, FERM BP-4249 |
| *Rhodophyllus clypeatus* | FERM BP-4589 |
| *Gloeophyllum sepiarium* | FERM BP-28 |
| *Fomes fomentarius* | FERM BP-30 |
| *Elfvingia applanata* | FERM BP-18 |
| *Fomitopsis pinicola* | FERM BP-26 |
| *Armillariella mellea* | FERM BP-281 |
| *Lampteromyces iaponicus* | FERM P-984, FERM BP-4939 |
| *Tricholoma matsutake* | FERM BP-4591 |

Any synthetic or natural medium composed of carbon and nitrogen sources, inorganic salts, vitamins and the other nutrients can be used for the cultivation of microorganisms of the present invention. Conventional sources such as glucose, sucrose, lactose, fructose, glycerol, starch and wasted molasses can be used as carbon sources, and trehalose may be used also for inducible strains.

Inorganic nitrogen compounds such as ammonium sulfate, ammonium nitrate, ammonium chloride, diammonium hydrogen-phosphate and urea, and organic nitrogen sources such as yeast extract, meat extract, peptone, casamino acid, corn steep liquor and soy bean meal can be used. In addition, inorganic salts such as potassium, sodium, magnesium, phosphate, and iron salts and a minute amount of metal salts can be used. Culture of the above mentioned microorganisms may be carried out in culture media for fruiting body of Basidiomycetes, for example saw dust, rice bran and barnyard manure can also be used. Various surface active agents may be used as antifoamers.

The culture is carried out at about 20°–40° C., preferably at 25°–35° C. and at initial pH of 4.5–8.0, preferably 5.0–7.0 by liquid shaking culture or aeration-agitation culture in jar fermenter. Furthermore, stand culture or solid culture may be applied.

Preparation of trehalose phosphorylase from enzyme sources is performed as follows. The enzyme generally exists within cells, thus cultured cells are preferably collected by centrifugation or filtration. The isolation and purification of trehalose phosphorylase from the cells is performed by collection of cells with centrifugation, washing of the collected cells with a buffer, suspension of washed cells in a buffer and followed by disruption of cells. The cell disruption is performed with conventional sonication, Waring Blendor™ (Dynamics Corp. of America, U.S.A.), rotation with glass beads in Dynomill Crusher, or decomposition of cell membrane with an enzyme such as lysozyme or an organic solvent such as toluene. After cell disruption, insoluble matters are separated and removed to give a crude enzyme solution. The crude enzyme solution can be used for the preparation of trehalose or α-D-glucose 1-phosphate as it is, but further isolation and purification may be performed.

Methods for isolation and purification of the crude enzyme solution was performed with those of common isolation and purification procedures for protein, such as salting out with ammonium sulfate or solvent precipitation, adsorption on an ion exchange resin, separation through a dialysis membrane, condensation with an ultrafiltration membrane, adsorption on hydroxyapatite, isolation with a hydrophobic carrier, or affinity chromatography. The resultant purified enzyme or crude enzyme may be used as it is, but immobilized enzyme prepared by known methods such as binding with a carrier, crosslinking, and gel entrapment, micro-encapsulation may also be used. Furthermore, immobilized living microorganisms by entrapment using polyacrylamide, κ-carageenan, alginic acid, and photo-crosslinking resin prepolymer may be applied as biocatalysts.

The activity of the enzyme is determined by the following procedure. That is, a total 100 ml buffer solution of 57 mM potassium phosphate containing 10.8 g of trehalose, 860 mg of glutathione and 17.2 mg of EDTA·2Na, pH 7.0, is prepared. A mixture of 1,400 µl of the buffer solution, 100 µl of 20 mM $NADP^+$ aqueous solution, 100 µl of 26 mM $MgCl_2$ aqueous solution, 100 µl of 1.34 mM glucose 1,6-diphosphate aqueous solution, 100 µl of 31 U/ml phosphoglucomutase aqueous solution, 100 µl of 35 U/ml glucose-6-phosphate dehydrogenase aqueous solution and 100 µl of a test sample enzyme solution is incubated at 30° C. and the amount of NADPH produced is determined by the absorbance at 340 nm with the passage of lime. The quantity of enzyme which produces one µ mole of NADPH in one minute under the above reaction conditions is made one Unit.

The specific activity of completely purified trehalose phosphorylase of the present invention is about 3.6 Unit/mg protein and shows a single protein band in sodium dodecyl-sulfate polyacrylamide gel electrophoresis (SDS-PAGE).

For the preparation of trehalose from α-D-glucose 1-phosphate and D-glucose with trehalose phosphorylase of the present invention, 5 mM to 4M, preferably 50 mM to 3M of α-D-glucose 1-phosphate and 5 mM to 4M, preferably 50 mM to 3M of D-glucose are caused to react in the presence of trehalose phosphorylase of the present invention at pH 2–10, preferably pH 4–9, and at reaction temperature of 10°–80° C., preferably 15°–50° C. 0.01 Unit or over, preferably 1–100 Unit of trehalose phosphorylase is used for one gram of substrate D-glucose. There is no upper limit in the amount of enzyme for the determination and an optimal amount can be determined in consideration of economic point of view.

For the preparation of α-D-glucose 1-phosphate from trehalose with trehalose phosphorylases of the present invention, 5 mM to 3M, preferably 50 mM to 2M of trehalose, 5 mM to 3M, preferably 50 mM to 2M of an inorganic phosphoric acid and/or its salt are caused to react in the presence of trehalose phosphorylase at pH 2–10, preferably pH 4–9, and at reaction temperature of 10°–80° C., preferably 15°–50° C. Trehalose phosphorylase is used at 0.01 Unit or over, preferably 1–100 Unit for one gram of substrate trehalose. There is no upper limit in the amount of enzyme for the determination and an optimal amount can be determined in consideration of economic point of view.

Inorganic phosphoric acids and/or their salts used the present invention include common inorganic phosphoric acids and salts thereof such as orthophosphoric acid, sodium phosphate, potassium phosphate, sodium dihydrogenphosphate and potassium dihydrogenphosphate, and preferably used as a phosphate buffer solution.

As explained above, the present invention provides thermally stable trehalose phosphorylases. The present invention also provides methods for the production of trehalose phosphorylase by the trehalose phosphorylase producing microorganisms which were newly found to produce trehalose phosphorylase and/or thermally stable trehalose phosphorylase. Furthermore, the present invention provides a process for the production of α-D-glucose 1-phosphate and trehalose with these trehalose phosphorylase.

The present invention will be practically explained by the following examples, however, the scope of the present invention is not restricted by these examples.

EXAMPLE 1

In 300 ml volume Erlenmeyer flasks, 100 ml of a medium composed of 0.75% of yeast extract, 0.2% of malt extract, 0.5% of potassium dihydrogenphosphate, 0.05% of magnesium sulfate and 4% of glucose (pH 5.5), was poured and pasteurized at 120° C. for 20 min. In 100 ml each of the pasteurized medium in three 300 ml volume Erlenmeyer flasks, *Coriolus hirsutus* ATCC 20561 (FERM P-2711) was inoculated and cultured with shaking at 26° C. for five days. The cultured mixture was centrifuged to collect mycelia, and the collected mycelia were suspended in 20 mM phosphate buffer. The mycelia in the suspension were disrupted with Waring Blendor™ (Dynamics Corp. of America, U.S.A.) and insoluble matters were removed by centrifugation to give 230 ml of crude enzyme solution. The crude enzyme solution showed trehalose phosphorylase activity of 0.075 Unit/ml and 17 Unit in total

EXAMPLE 2

Various strains shown in Table 2 were inoculated in the defined media (100 ml medium in two 300 ml Erlenmeyer flasks for one strain), prepared by the similar manner to that of Example 1 and cultured with shaking at 26° C. for 5–20 days. The cultured mixture was treated in a similar manner to that of Example 1 to give crude enzyme solution. The volume of each crude enzyme solution, trehalose phosphorylase activity and total activity thereof are shown in Table 2.

TABLE 2

| Strain | Vol of medium (ml) | Activity (Unit/ml) | Total activity (Unit) |
| --- | --- | --- | --- |
| *Grifola frondosa* FERM BP-35 | 25 | 0.12 | 2.9 |
| *Pleurotus ostreatus* (FERM P-1746), FERM BP-4951 | 64 | 0.17 | 11 |
| *Lyophyllum ulmarium* (FERM P-985), FERM BP-4940 | 16 | 0.009 | 0.14 |
| *Lentinus edodes* FERM BP-947 | 15 | 0.012 | 0.19 |
| *Coriolus consors* (FERM P-988), ATCC 20565 | 53 | 0.008 | 0.43 |
| *Schizophyllum commune* (FERM P-1744), FERM BP-4941 | 114 | 0.047 | 5.4 |
| *Panus rudis* FERM BP-4588 | 76 | 0.033 | 2.5 |
| *Crepidotus variabilis* (FERM P-5161), FERM BP-4943 | 132 | 0.099 | 13 |
| *Naematoloma sublateritium* (FERM P-3051), FERM BP-4942 | 59 | 0.006 | 0.36 |
| *Rhodophyllus clypeatus* FERM BP-4589 | 49 | 0.015 | 0.73 |
| *Gloeophyllum sepiarium* FERM BP-28 | 24 | 0.008 | 0.19 |
| *Fomes fomentarius* FERM BP-30 | 41 | 0.026 | 1.1 |
| *Elfvingia applanata* FERM BP-18 | 31 | 0.039 | 0.12 |
| *Fomitopsis pinicola* FERM BP-26 | 27 | 0.007 | 0.18 |
| *Armillariella mellea* FERM BP-281 | 138 | 0.007 | 0.93 |
| *Lampteromyces japonicus* (FERM P-984), FERM BP-4939 | 30 | 0.016 | 0.46 |
| *Favolus arcularius* FERM BP-4590 | 130 | 0.051 | 6.6 |
| *Pleurotus cornucopiae* | 87 | 0.035 | 3.0 |

TABLE 2-continued

| Strain | Vol of medium (ml) | Activity (Unit/ml) | Total activity (Unit) |
| --- | --- | --- | --- |
| IFO 30528 | | | |
| *Laetiporus sulphureus* IFO 8406 | 80 | 0.003 | 0.23 |
| *Laetiporus versisporus* IFO 9043 | 32 | 0.003 | 0.082 |
| *Polyporellus picipes* IFO 30355 | 69 | 0.004 | 0.29 |
| *Oudemansiella canarii* IFO 31246 | 62 | 0.005 | 0.28 |
| *Pholiota adiposa* IFO 9779 | 76 | 0.062 | 4.7 |

EXAMPLE 3

In 300 ml Erlenmeyer flasks, 100 ml of a medium composed of 0.75% of yeast extract and 5.0% of glucose (pH 5.5), were poured and pasteurized at 120° C. for 20 min. In 100 ml each of the pasteurized medium poured in 300 ml volume Erlenmeyer flasks, microorganisms shown in Table 3 were inoculated and cultured with shaking at 26° C. for three days. The cultured mixture was centrifuged to collect mycelia, and the collected mycelia were suspended in 200 ml of 20 mM phosphate buffer. The mycelia in the suspension were disrupted with Waring Blendor™ (Dynamics Corp. of America, U.S.A.) and insoluble matters were removed by centrifugation to give a crude enzyme solution. The crude enzyme solution was poured into a column of 20 ml of DEAE Toyopearl™ 650C (TOSOH Corp.) equilibrated with 20mM phosphate buffer, washed with the same buffer, eluted with 400 ml linear gradient of 0–0.5M potassium chloride in 20 mM phosphate buffer, and fractionated about seven milliliters each eluate. The active fractions were combined to give an enzyme solution. The volume of enzyme solution derived from each microorganism and trehalose phosphorylase activity, total activity and specific activity thereof are shown in Table 3.

TABLE 3

| Strain | Volume (ml) | Activity (Unit/ml) | Total activity (Unit) | Specific activity (Unit/mg protein) |
| --- | --- | --- | --- | --- |
| *Coriolus versicolor* FERM P-2412 ATCC 20547 | 73 | 0.084 | 6.1 | 0.14 |
| *Coriolus hirsutus* FERM P-2711 ATCC 20561 | 69 | 0.071 | 4.9 | 0.23 |
| *Trichaptum biforme* FERM P-2712 ATCC 20562 | 51 | 0.071 | 3.6 | 0.086 |
| *Lenzites betulina* FERM BP-27 | 35 | 0.11 | 3.9 | 0.35 |

EXAMPLE 4

In a 200 L volume of jar fermenter, *Schizophyllum commune* FERM BP-4941 (FERM P-1744) was inoculated and cultured in 100 L medium composed of 0.75% of yeast extract, 0.2% of malt extract and 5% of glucose (pH 6.2), at 25° C., 290 rpm stirring, and aeration rate of 0.5 VVM for 70 hrs. After the culture, mycelia in 400 ml of cultured mixture were collected by centrifugation.

Collected mycelia were suspended in about 200 ml of 20 mM phosphate buffer (pH 7.0), disrupted with Waring Blendor (Dynamics Corp. of America, U.S.A.) and insoluble matters were removed by centrifugation to give about 240 ml of a crude enzyme solution. The crude enzyme solution was poured into a column of 20 ml of DEAE Toyopearl™ 650C (TOSOH Corp.) equilibrated with 20 mM phosphate buffer, washed with the same buffer, eluted with 400 ml linear gradient of 0–0.5M potassium chloride in 20 mM phosphate buffer fractionated about 7.5 ml each eluate to give 80 ml of active fraction. The trehalose phosphorylase activity, total activity and specific activity in the active fraction were 0.13 Unit/ml, 10.3 Unit and 0.15 Unit/mg protein, respectively.

EXAMPLE 5

In about 150 ml each of 20 mM phosphate buffer containing 20% of glycerol, and one millimole each of EDTA and dithiothreitol (pH 7.0), 100 g of fresh fruiting body selected from the group consisting of *Agaricus bisporus, Grifola frondosa, Tricholoma matsutake, Pleurotus ostreatus, Lyophyllum ulmarium* or *Lentinus edodes* was added and disrupted with Waring Blendor™ (Dynamics Corp. of America, U.S.A.) and insoluble matters were removed by centrifugation to give a supernatant of crude enzyme solution.

The crude enzyme solution was poured into a column of 20 ml of QAE Toyopearl™ (TOSOH Corp.) equilibrated with 20 mM phosphate buffer, washed with the same buffer, eluted with 400 ml linear gradient of 0–0.5M potassium chloride in 20 mM phosphate buffer. Trehalose phosphorylase active fractions were combined and concentrated with a hollow fiber ultrafiltration apparatus to give each enzyme solution. The volume of enzyme solution derived from each microorganism and trehalose phosphorylase activity, total activity and specific activity thereof are shown in Table 4.

TABLE 4

| Strain | Volume (ml) | Activity (Unit/ml) | Total activity (Unit) | Specific activity (Unit/mg protein) |
| --- | --- | --- | --- | --- |
| Agaricus bisporus | 4.0 | 2.4 | 9.5 | 0.13 |
| Grifola frondosa | 10 | 4.75 | 48 | 0.37 |
| Tricholoma matsutake | 7.8 | 0.010 | 0.082 | 0.0034 |
| Pleurotus ostreatus | 5.3 | 5.1 | 27 | 0.45 |
| Lyophyllum ulmarium | 10 | 0.56 | 5.6 | 0.027 |
| Lentinus edodes | 6.7 | 0.04 | 0.27 | 0.0032 |

EXAMPLE 6

In about 600 ml of 20 mM phosphate buffer containing 20% of glycerol, and 1 mM EDTA and 1 mM dithiothreitol (pH 7.0), 300 g of fresh fruiting body of *Grifola frondosa* was added and crushed with Waring Blendor™ (Dynamics Corp. of America, U.S.A.) and insoluble matters were removed by centrifugation to give 758 ml of a supernatant of crude enzyme solution. The crude enzyme solution showed total activity of 185 Unit, specific activity of 0.038 Unit/mg protein.

In the crude enzyme solution, ammonium sulfate was added to give 40% saturation, the formed insoluble matters were removed by centrifugation, further ammonium sulfate was added to give 60% saturation, and the precipitates of 60% ammonium sulfate saturation were collected by centrifugation. The precipitates were dissolved in a small amount of 20 mM phosphate buffer containing 20% ammonium sulfate and poured into a column of Butyl Toyopearl™ (TOSOH Corp.) equilibrated with the same buffer, 22 mm in diameter and 250 mm in length. The column was washed with the same buffer and eluted with 800 ml linear gradient of 20–0% of ammonium sulfate in 20 mM phosphate buffer to give fractions each weighing 10 g. The enzymic activity was found in fraction Nos. 64–78.

The combined active fractions were concentrated and poured into a column of Toyopearl™ HW-55S (TOSOH Corp.) equilibrated with 20 mM phosphate buffer, 25 mm in diameter and 700 mm in length, and eluted to give each 10 ml volume of active fraction Nos. 16–20. The combined active fractions were poured into a column of DEAE Toyopearl™ 650C (TOSOH Corp.) equilibrated with 20 mM phosphate buffer, 22 mm in diameter and 250 mm in length. The column was eluted with 800 ml linear gradient of 0–0.3M potassium chloride in 20 mM phosphate buffer to give 10 ml each fractions, and active fraction Nos. 23–34 were obtained. The combined active fractions showed trehalose phosphorylase activity of 0.93 Unit/ml, total activity of 111 Unit and specific activity of 2.64 Unit/mg protein.

The combined active fractions were dialyzed against 20 mM phosphate buffer and poured in AF-blue Toyopearl™ 650ML (TOSOH Corp.) column of 10 mm in diameter and 150 mm in length equilibrated with 20 mM phosphate buffer. The column was eluted with 400 ml linear gradient of 0–0.5M potassium chloride in 20 mM phosphate buffer to give 10 ml each fractions, and active fraction Nos. 13–40 were obtained. The combined active fractions were purified by high performance liquid chromatography (HPLC) using TSK gel™ G3000SW (TOSOH Corp.) column, 7.5 cm in diameter and 300 mm in length, equilibrated with 20 mM phosphate buffer, at a flow rate of 0.5 ml/min.

The purified fraction showed one active peak at 15.9 min. by detection at UV 280 nm. The presumed molecular weight from retention time of the active peak and that of standard protein was about 120,000. The activity, total activity and specific activity of the purified enzyme was 3.57 Unit/ml, 18 Unit and 5.63 Unit/mg protein, respectively. Analysis of the resultant enzyme analyzed by SDS-PAGE revealed single band indicating a pure trehalose phosphorylase having molecular weight of about 60,000.

EXAMPLE 7

The substrate specificity, optimal reaction pH, pH stability, optimal reaction temperature, and thermal stability of the purified enzyme obtained in Example 6 and the purified enzymes prepared according to the method of Example 6 were determined. The quantitative determination of α-D-glucose 1-phosphate and trehalose was carried out by the following method.

Quantitative determination of α-D-glucose 1-phosphate: Fifty μl of the test sample solution were mixed with 120 μl of 0.5M phosphate buffer (pH 7.0), 150 μl of 1.0M HEPES buffer (pH 7.0), 50 μl of 14.8 mM NADP$^+$ aqueous solution, 50 μl of 26mM MgCl$_2$ aqueous solution and 50 μl of 1.34 mM α-D-glucose 1,6-diphosphate aqueous solution, 25 μl of 31 Unit/ml aqueous solution of phosphoglucomutase (0.78 Unit), and 25 μl of 35 Unit/ml aqueous solution of glucose-6-phosphate dehydrogenase (0.88 Unit), and 980 μl of purified water, and incubated at 30° C. for 30 min., then the amount of formed NADPH was determined at 340 nm to give the amount of α-D-glucose 1-phosphate.

Quantitative Determination of Trehalose:

The concentration of trehalose in the reaction mixture was determined by high performance liquid chromatography (HPLC) using a polyamine column (YMC Pack™, Polyamine II, 4.6 mm in diameter and 250 mm in length, YMC Co., Ltd.), elution solution of a mixture of acetonitrile:water=70:30, flow rate of one ml/min., column temperature of 35° C. and a differential refractometer at cell temperature of 35° C.

The retention time of trehalose under these HPLC conditions was 15.7 min.

[Substrate Specificity]

Phosphorolytic Reaction:

Phosphorolytic reaction of various sugars were performed with the enzyme of the present invention. Trehalose gave α-D-glucose 1-phosphate and D-glucose. No disaccharide other than trehalose, such as paratinose, maltose, isomaltose, sucrose, lactose, cellobiose or neotrehalose showed reactivity with the enzyme.

Disaccharide Synthetic Reaction:

Disaccharide synthetic reaction from various monosaccharides and α-D-glucose 1-phosphate was performed with the enzyme of the present invention. No reaction was observed in L-glucose, D-galactose, D-mannose, D-xylose, D-fructose, D-sorbitol, D-mannitol or D-fucose except for D-glucose. Reactions of D-glucose and various sugar phosphates with the enzyme of the present invention were carried out. No β-D-glucose 1-phosphate, α-D-mannose 1-phosphate, α-D-xylose 1-phosphate or a -D-galactose 1-phosphate showed reactivity with the enzyme except for α-D-glucose 1-phosphate.

[Optimal pH]

Phosphorolytic Reaction

Acetate buffer (pH 4.0–5.5), MES buffer (pH 5.5–7.0), HEPES buffer (pH 7.0–8.2) and glycine-NaOH buffer (pH 8.5–9.7) were used. The reaction was performed at 30° C. for one hour at these pHs and the formed quantity of α-D-glucose 1-phosphate was determined to give the enzymic activity. The results showed that the optimal pH range of the enzymic reaction was 5.5–7.5. The relative activity was calculated on the basis of the maximum activity which was made 100% and graphed in FIG. 1.

Figure 2:
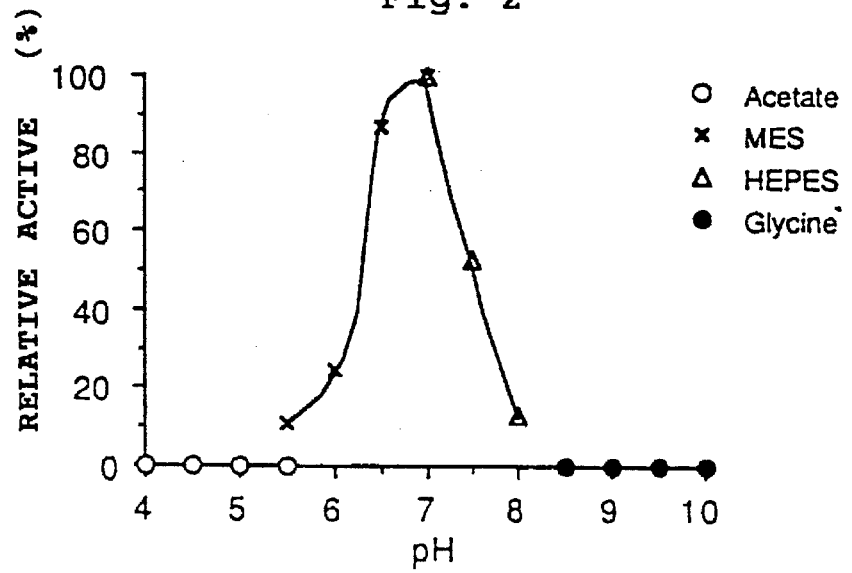
FIG. 2 shows the optimal pH range for the synthetic reaction of trehalose with the trehalose phosphorylases of the present invention.

Trehalose Synthetic Reaction:

Acetate buffer (pH 4.0–5.5), MES buffer (pH 5.5–7.0), HEPES buffer (pH 7.0–8.0) and glycine-NaOH buffer (pH 8.5–11.0) were used. The reaction was performed at 35° C. for three hours at these pHs and the formed quantity of trehalose was determined to give the enzymic activity. The results showed that the optimal pH range of the enzymic reaction was 6.5–7.5. The relative activity was calculated on the basis of the maximum activity which was made 100% and graphed in FIG. 2.

[pH Stability]

Phosphorolytic Reaction

Figure 3:
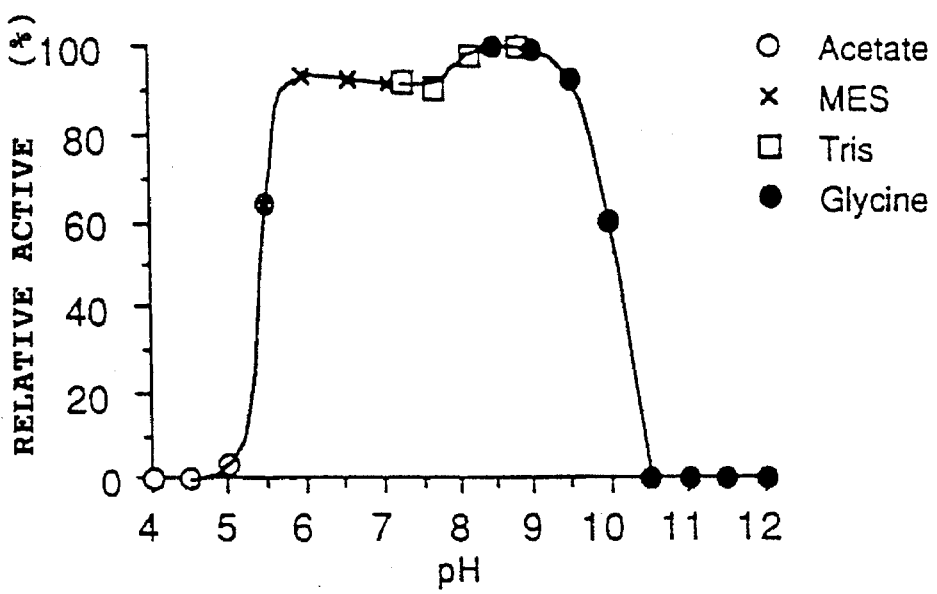
FIG. 3 shows the stable pH range for the phosphorolysis of trehalose phosphorylases of the present invention.

Acetate buffer (pH 4.0–5.5), MES buffer (pH 5.5–7.0), Tris-HCl buffer (pH 7.5–9.0) and glycine-NaOH buffer (pH 8.5–12.0) were used. Trehalose phosphorylase was allowed to stand at 4° C. for 24 hours at these pHs, further caused to react at 32.5° C. for one hr., and the quantity of α-D-glucose 1-phosphate formed was determined by the method shown above to give the enzymic activity at various pHs. The results showed that the enzyme is stable at pH 5.5–9.5. The relative activity was calculated on the basis of the maximum activity which was made 100% and graphed in FIG. 3.

Figure 4:
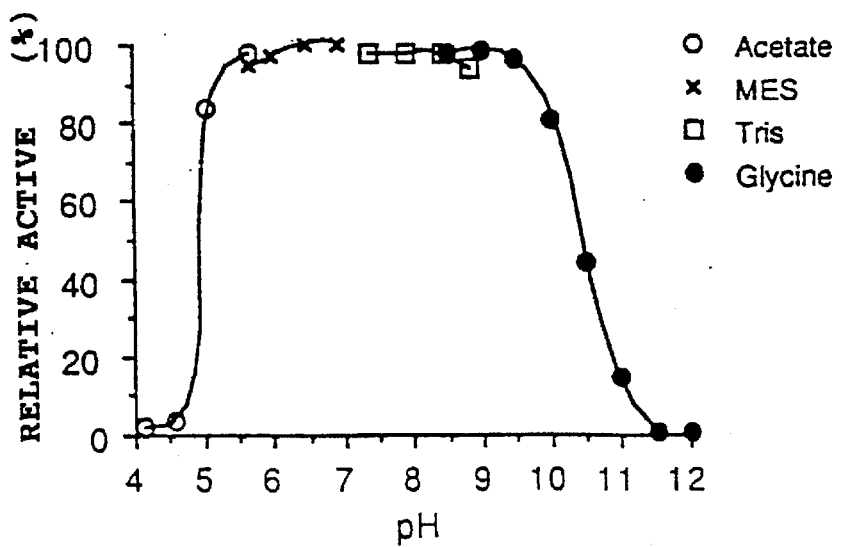
FIG. 4 shows the stable pH range for the synthetic reaction of trehalose with the trehalose phosphorylases the present invention.

Trehalose synthetic reaction:

Acetate buffer (pH 4.0–5.5), MES buffer (pH 5.5–7.0), Tris-HCl buffer (pH 7.5–9.0) and glycine-NaOH buffer (pH 8.5–12.0) were used. Trehalose phosphorylase was allowed to stand at 4° C. for 24 hours at these pHs, further caused to react at 35° C. for three hrs., and the quantity of trehalose formed was determined by the HPLC method shown above to give the enzymic activity at various pHs. The results showed that the enzyme is stable in a range of pH 5.0–10.5. The relative activity was calculated on the basis of the maximum activity which was made 100% and graphed in FIG. 4.

[Optimal Reaction Temperature]

Figure 5:
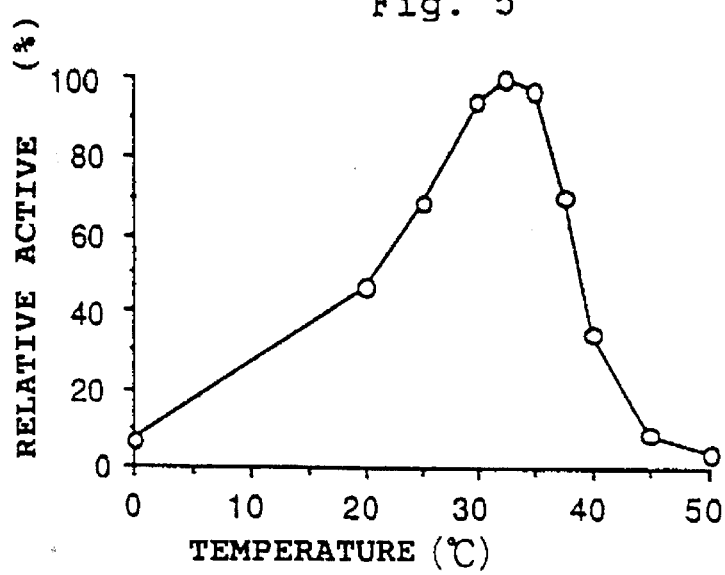
FIG. 5 shows the optimal temperature range for the phosphorolysis with the trehalose phosphorylases of the present invention.

Phosphorolytic Reaction:

In MES buffer (pH 6.0), the reaction was carried out at desired temperatures between 0° and 50° C. for one hour and the enzyme was inactivated by heating. Then the amount of the produced α-D-glucose 1-phosphate was determined by the method shown above to give the enzymic activity at the tested temperatures. The results showed the optimal reaction temperature of 25°–37.5° C. The relative activity was calculated on the basis of the maximum activity which was made 100% and graphed in FIG. 5.

Figure 6:
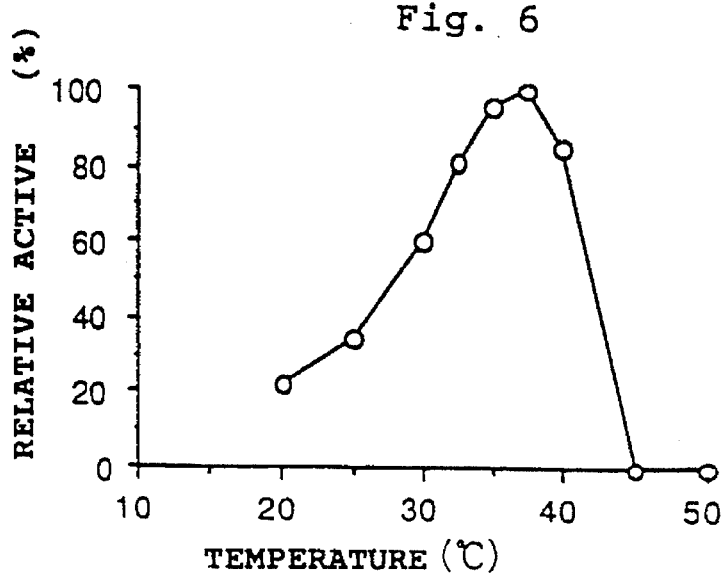
FIG. 6 shows the optimal temperature range for the synthetic reaction of trehalose with the trehalose phosphorylases of the present invention.

Trehalose Synthetic Reaction:

In HEPES buffer (pH 7.0), the reaction was carried out at desired temperatures between 20° and 50° C. for three hours and the enzyme was inactivated by heating. Then, the amount of the produced trehalose was determined by the HPLC method shown above to give the enzymic activity at tested temperatures. The results showed the optimal reaction temperatures of 30°–40° C . The relative activity was calculated on the basis of the maximum activity which was made 100% and graphed in FIG. 6.

[Thermal Stability]

Figure 7:
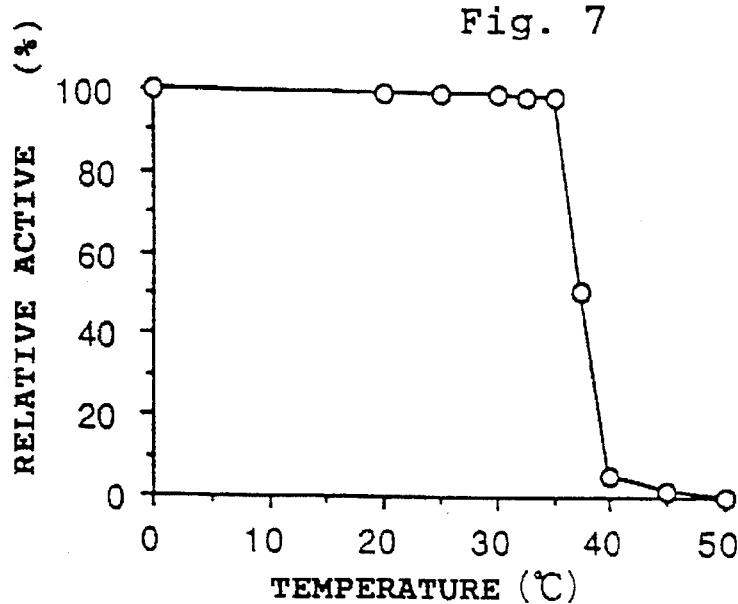
FIG. 7 shows the thermal stability of the trehalose phosphorylases of the present invention in the phosphorolysis.

Phosphorolytic Reaction:

In 20 mM phosphate buffer (pH 7.0), trehalose phosphorylase was allowed to stand at desired temperatures between 0° and 50° C. for 30 min. and to react at 32.5° C. for one hour and was inactivated by heating. The amount of the produced α-D-Glucose 1-phosphate was determined by the method shown above to give the enzymic activity at temperatures tested. The results showed the enzyme was stable up to 35° C. The relative activity was calculated on the basis of the maximum activity which was made 100% and graphed in FIG. 7.

Figure 8:
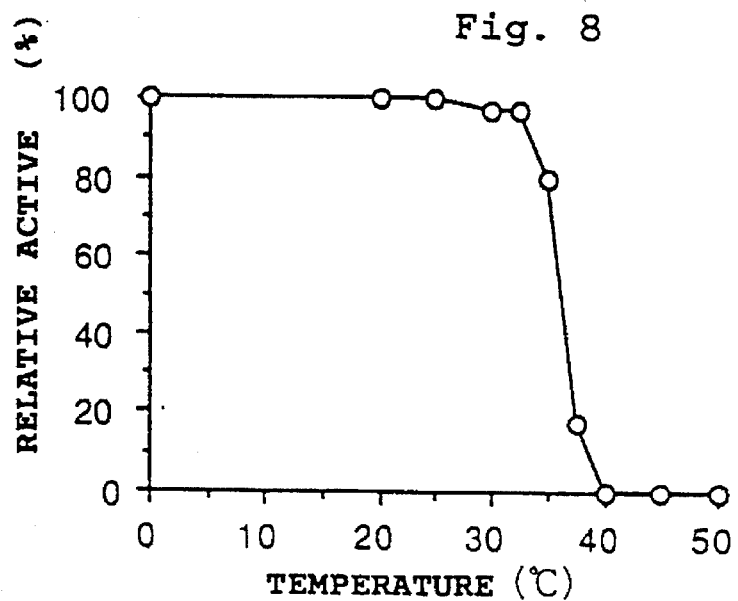
FIG. 8 shows the stable temperature range for the synthetic reaction of trehalose with the trehalose phosphorylases of the present invention.

Synthetic Reaction of Trehalose:

In 20 mM phosphate buffer (pH 7.0), the enzyme was allowed to stand at a desired temperatures between 0° and 50° C. for 30 min. and to react at 35° C. for three hours and was inactivated by heating. The amount of the produced trehalose was determined by the HPLC method shown above to give the enzymic activity at temperatures tested. The results showed the enzyme was stable up to 35° C. The relative activity was calculated on the basis of the maximum activity which was made 100% and graphed in FIG. 8.

EXAMPLE 8

A trehalose phosphorylase solution obtained from *Schizophyllum commune* FERM BP-4941 (FERM P-1744) in Example 4 was concentrated with a hollow fiber ultrafiltration apparatus to 12 ml of an enzyme solution. The activity of the enzyme solution was 0.87 Unit/ml. A mixture of 10 μl of the enzyme solution, 125 μl of 0.4M D-glucose aqueous solution and 125 μl of 0.4M α-D-glucose 1-phosphate, 100

μl of 0.5M MES buffer solution (pH 7.0), and 140 μl of purified water was incubated at 30° C. for 24 hrs. in an Epfendorf tube. The enzyme was inactivated by heating and the quantitative determination of trehalose according to the method described in Example 7 indicated the concentration of 11 mM. The yield of trehalose from D-glucose was 11%.

EXAMPLE 9

Trehalose synthetic reaction was carried out using trehalose phosphorylase solutions derived from *Agaricus bisporus, Grifola frondosa, Pleurotus ostreatus* and *Lyophyllum ulmarium* according to Example 5 in a similar manner to that of Example 8 and the concentration of trehalose in the reaction mixture was determined in a similar manner to that of Example 7. The concentrations of trehalose were 24, 35, 48, and 7.4 mM, respectively. The molar yields of trehalose from D-glucose were 24, 35, 48 and 7%, respectively.

EXAMPLE 10

A mixture of 56 μl of 3.57 Unit/ml aqueous solution of purified trehalose phosphorylase (0.2 Unit) derived from *Grifola frondosa* in Example 6, 100 μl of 1.0M HEPES buffer (pH 7.0), 150 μl of 1.0M D-glucose aqueous solution, 400 μl of 0.5M α-D-glucose 1-phosphate and 294 μl of purified water was incubated at 35° C. for 72 hrs. in an Epfendorf tube. The enzyme was inactivated by heating and the concentration of trehalose in the reaction mixture was determined by the method described in Example 7 and 80 mM of trehalose was found. The molar yield of trehalose from D-glucose was 53%.

EXAMPLE 11

A mixture of 28 μl of 3.57 Unit/ml aqueous solution of purified trehalose phosphorylase (0.2 Unit) derived from *Grifola frondosa* in Example 6, 200 μl of 0.5M trehalose aqueous solution, 250 μl of 0.4M phosphate buffer (pH 6.5), 200 μl of 0.5M MES buffer (pH 6.5), and 322 μl of purified water was incubated at 30° C. for 24 hrs. in an Epfendorf tube. The enzyme was inactivated by heating and the concentration of α-D-glucose 1-phosphate in the reaction mixture was determined by the method described in Example 7 and 32 mM of α-D-glucose 1-phosphate was found. The molar yield of α-D-glucose 1-phosphate from trehalose was 32%. Determination of D-glucose in the reaction mixture with a glucose determination kit (Iatochrome™ Glu-L$^Q$, Iatron Co., Ltd.) showed D-glucose concentration of 31 mM.

We claim:

1. An isolated trehalose phosphorylase enzyme produced by a microorganism selected from the group consisting of Grifola, Pleurotus, Lyophyllum, Lentinus, Agaricus, Trametes, Coriolus, Lenzites, Schizophyllum, Panus, Crepidotus, Laetiporus, Polyporellus, Favolus, Trichaptum, Oudemansiella, Naematoloma, Rhodophyllus, Gloeophyllum, Fomes, Ganoderma, Elfvingia, Fomitopsis, Armillariella, Lampteromyces, Pholiota and Tricholoma genera, which enzyme catalyzes the reaction of trehalose with inorganic phosphoric acid or salt thereof to produce α-D-glucose 1-phosphate and D-glucose, and the reaction of α-D-glucose 1-phosphate with D-glucose to produce trehalose and an inorganic phosphoric acid, and wherein the enzyme has a molecular weight of about 120,000 daltons as determined by gel filtration and about 60,000 daltons as determined by SDS-PAGE.

2. The trehalose phosphorylase enzyme according to claim 1 which catalyzes the reaction of α-D-glucose 1-phosphate with D-glucose to produce trehalose and inorganic phosphoric acid utilizing the following reaction conditions:

Optimal reaction pH: about 6.5–7.5 at 35° C., pH stability: stable in the range of about pH 5.0–10.5 at about 4° C. for about 24 hrs., Optimal reaction temperature: about 30°–40° C. at about pH 7.0, and Thermal stability: stable at temperatures of about 35° C. at pH 7.0 for about 30 min.

3. The trehalose phosphorylase enzyme according to claim 1 produced by a microorganism selected from the group consisting of *Grifola frondosa, Pleurotus ostreatus, Pleurotus cornucopiae, Lyophyllum ulmarium, Lentinus edodes, Agaricus Bisporus, Coriolus consors, Coriolus versicolor, Coriolus hirsutus, Trametes versicolor, Trametes hirsuta, Lenzites betulina, Schizophyllum commune, Panus rudis, Crepidotus variabilis, Laetiporus sulphureus, Laetiporus versisporus, Polyporellus picipes, Favolus arcularius, Coriolus pargamenus, Trichaptum biforme, Oudemansiella canarii, Naematoloma sublateritium, Rhodophyllus clepeatus, Gloeophyllum sepiarium, Fomes fomentarius, Ganoderma applanatum, Elfvingia applanata, Fomitopsis pinicola, Armillariella mellea, Lampteromyces japonicus, Pholiota adiposa* and *Tricholoma matsutake*, which enzyme catalyzes the reaction of trehalose with an inorganic phosphoric acid or salt thereof to produce α-D-glucose 1-phosphate and D-glucose, and the reaction of α-D-glucose 1-phosphate with D-glucose to produce trehalose and an inorganic phosphoric acid.

4. The isolated trehalose phosphorylase enzyme according to claim 1 or 3, wherein the enzyme is produced by mutants of the microorganism or induced strains of the microorganism which have been transformed by gene manipulation.

5. The trehalose phosphorylase enzyme according to claim 2 which catalyzes the reaction of trehalose with inorganic phosphoric acid or a salt thereof, to produce α-D-glucose 1-phosphate and D-glucose utilizing the following reaction conditions:

Optimal reaction pH: from about 5.5 to about 7.5 at 30° C.,

Optimal reaction temperature: from about 25° C. to about 37.5° C. at about pH 6.0.

* * * * *